United States Patent
Mabuchi

(10) Patent No.: US 9,550,889 B2
(45) Date of Patent: Jan. 24, 2017

(54) TRUCK OR BUS TIRES

(71) Applicant: SUMITOMO RUBBER INDUSTRIES, LTD., Kobe-shi, Hyogo (JP)

(72) Inventor: Takahiro Mabuchi, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 0 days.

(21) Appl. No.: 14/714,516

(22) Filed: May 18, 2015

(65) Prior Publication Data

US 2015/0361252 A1 Dec. 17, 2015

(30) Foreign Application Priority Data

Jun. 16, 2014 (JP) ................................ 2014-123594

(51) Int. Cl.

| | |
|---|---|
| *C08L 7/00* | (2006.01) |
| *C12P 5/00* | (2006.01) |
| *C08L 9/06* | (2006.01) |
| *B60C 1/00* | (2006.01) |
| *C08K 3/04* | (2006.01) |
| *C08K 3/36* | (2006.01) |

(52) U.S. Cl.
CPC . *C08L 7/00* (2013.01); *B60C 1/00* (2013.01); *B60C 1/0016* (2013.04); *C12P 5/007* (2013.01); *C08L 2205/02* (2013.01); *C08L 2205/03* (2013.01); *Y02T 10/862* (2013.01)

(58) Field of Classification Search
CPC ..... C08L 7/00; C08L 2205/02; C08L 2205/03; C12P 5/007; C08K 3/04; C08K 3/36; B60C 1/00
USPC ........................................................ 524/493
See application file for complete search history.

(56) References Cited

U.S. PATENT DOCUMENTS

2014/0155536 A1* 6/2014 Kuwahara ............ C08F 136/22
524/496
2015/0057392 A1* 2/2015 Koda ........................ B60C 1/00
523/156

FOREIGN PATENT DOCUMENTS

| | | | |
|---|---|---|---|
| EP | 2 810 963 A1 | 12/2014 | |
| EP | 2 835 383 A1 | 2/2015 | |
| JP | 2001-114939 A | 4/2001 | |
| JP | 2005-126604 A | 5/2005 | |
| JP | 2005-325206 A | 11/2005 | |
| JP | WO 2013115011 A1 * | 8/2013 | ........... B60C 1/0016 |
| JP | EP 2810963 A1 * | 12/2014 | ........... B60C 1/0016 |
| WO | WO 2012075216 A2 * | 6/2012 | ............... A23G 4/08 |
| WO | WO 2013047348 A1 * | 4/2013 | ........... C08F 136/22 |
| WO | WO 2013/115011 A1 | 8/2013 | |
| WO | WO 2013/151067 A1 | 10/2013 | |
| WO | WO 2013151067 A1 * | 10/2013 | ............... B60C 1/00 |

OTHER PUBLICATIONS

Fox et al., "Second-Order Transition Temperatures and Related Properties of Polystyrene. I. Influence of Molecular Weight", J. Appl. Phys., 21, 581-591 (1950).*

* cited by examiner

*Primary Examiner* — Ling Choi
*Assistant Examiner* — Ronald Grinsted
(74) *Attorney, Agent, or Firm* — Birch, Stewart, Kolasch & Birch, LLP

(57) ABSTRACT

The present invention provides truck or bus tires having an excellent balance of fuel economy, rubber strength, and abrasion resistance together with high productivity. The present invention relates to a truck or bus tire, including a cap tread formed from a rubber composition, the rubber composition containing a rubber component including at least one selected from the group consisting of polyisoprene rubbers and polybutadiene rubber, and, per 100 parts by mass of the rubber component, 10 to 60 parts by mass of a reinforcing filler and 1 to 20 parts by mass of a farnesene resin obtained by polymerizing farnesene.

12 Claims, No Drawings

TRUCK OR BUS TIRES

TECHNICAL FIELD

The present invention relates to truck or bus tires.

BACKGROUND ART

In recent years, the cost increases associated with rising fuel prices and introduction of environmental regulations have led to a need for tires with excellent fuel economy in the transportation business. In order to improve fuel economy, Patent Literatures 1 to 3 for example propose methods in which rubber to be used in a silica-containing composition is addition reacted with a specific polar group so that the rubber has an affinity for silica. Although the methods enhance the reaction efficiency between silica and rubber (polymer) to improve fuel economy, the methods tend to increase Mooney viscosity so that processability can be deteriorated. Moreover, there has been a recent demand for more improved fuel economy.

Furthermore, among automobile tires, truck or bus tires need to have particularly excellent abrasion resistance and rubber strength. However, these properties and fuel economy have a tradeoff relationship. Thus, methods are needed to achieve balanced improvements in processability, fuel economy, rubber strength, and abrasion resistance.

CITATION LIST

Patent Literature

Patent Literature 1: JP 2001-114939 A
Patent Literature 2: JP 2005-126604 A
Patent Literature 3: JP 2005-325206 A

SUMMARY OF INVENTION

Technical Problem

The present invention aims to solve the above problem and provide truck or bus tires having an excellent balance of fuel economy, rubber strength, and abrasion resistance together with high productivity.

Solution to Problem

The present invention relates to a truck or bus tire, including a cap tread formed from a rubber composition, the rubber composition containing a rubber component including at least one selected from the group consisting of polyisoprene rubbers and polybutadiene rubber, and, per 100 parts by mass of the rubber component, 10 to 60 parts by mass of a reinforcing filler and 1 to 20 parts by mass of a farnesene resin obtained by polymerizing farnesene.

The reinforcing filler is preferably at least one of carbon black and silica.

The farnesene resin is preferably a farnesene homopolymer.

The homopolymer preferably has a glass transition temperature of −60° C. or lower.

The homopolymer preferably has a weight average molecular weight of 3,000 to 500,000.

The homopolymer preferably has a melt viscosity at 38° C. of 1,000 Pa·s or lower.

The farnesene resin is preferably a copolymer of farnesene and a vinyl monomer.

The vinyl monomer is preferably styrene.

The vinyl monomer is preferably butadiene.

The copolymer preferably has a farnesene/vinyl monomer ratio of 99/1 to 25/75 by mass.

The copolymer preferably has a weight average molecular weight of 3,000 to 500,000.

The copolymer preferably has a melt viscosity at 38° C. of 1,000 Pa·s or lower.

Preferably, the farnesene is prepared by culturing a microorganism using a carbon source derived from a saccharide.

Advantageous Effects of Invention

The truck or bus tires of the present invention include a cap tread formed from a rubber composition prepared by adding to a specific rubber component predetermined amounts of a reinforcing filler and a farnesene resin obtained by polymerizing farnesene. Thus, the tires have an excellent balance of fuel economy, rubber strength, and abrasion resistance. Moreover, such a rubber composition has good processability, and therefore the truck or bus tires can be produced with high productivity.

DESCRIPTION OF EMBODIMENTS

The truck or bus tires of the present invention includes a cap tread formed from a rubber composition prepared by adding to a specific rubber component predetermined amounts of a reinforcing filler and a farnesene resin obtained by polymerizing farnesene. The addition of the farnesene resin as a softener to a composition containing the rubber component and the reinforcing filler results in a good balance of processability, fuel economy, rubber strength, and abrasion resistance.

The rubber composition according to the present invention contains a rubber component that includes at least one selected from the group consisting of polyisoprene rubbers and polybutadiene rubber (BR). If the rubber component includes a polyisoprene rubber, rubber strength can be enhanced, and the components in the rubber mixture are more likely to come together during kneading, so that productivity can be improved. Also, if the rubber component includes BR, balanced improvements in processability, fuel economy, rubber strength, and abrasion resistance can be achieved.

Examples of polyisoprene rubbers include natural rubber (NR) and polyisoprene rubber (IR). Non-limiting examples of NR include those commonly used in the tire industry, such as SIR20, RSS#3, TSR20, deproteinized natural rubber (DPNR), highly purified natural rubber (UPNR), and epoxidized natural rubber (ENR). Similarly, IR may be one commonly used in the tire industry. NR is especially preferred because it allows the effect of the present invention to be more suitably achieved.

In the case where the rubber composition according to the present invention contains a polyisoprene rubber, the amount of polyisoprene rubber based on 100% by mass of the rubber component is preferably 60% by mass or more, more preferably 65% by mass or more, particularly preferably 70% by mass or more. If the amount is less than 60% by mass, rubber strength may decrease, and the components in the rubber mixture are less likely to come together during kneading, so that productivity may be deteriorated.

The amount of polyisoprene rubber is also preferably 95% by mass or less, more preferably 90% by mass or less. If the amount is more than 95% by mass, abrasion resistance may be poor.

Examples of BR include those commonly used in the tire industry, including high-cis BR such as BR1220 available from ZEON Corporation and BR130B and BR150B available from Ube Industries, Ltd.; and BR containing syndiotactic polybutadiene crystals such as VCR412 and VCR617 available from Ube Industries, Ltd.

The BR preferably has a cis content of 95% by mass or more, more preferably 97% by mass or more.

The cis content values herein are calculated by infrared absorption spectrum analysis.

In the case where the rubber composition according to the present invention contains BR, the amount of BR based on 100% by mass of the rubber component is preferably 5% by mass or more, more preferably 10% by mass or more, still more preferably 15% by mass or more. If the amount is less than 5% by mass, abrasion resistance tends to decrease. The amount of BR is also preferably 40% by mass or less, more preferably 35% by mass or less, still more preferably 30% by mass or less. If the amount is more than 40% by mass, processability tends to decrease.

The combined amount of polyisoprene rubber and BR, based on 100% by mass of the rubber component, is preferably 80% by mass or more, more preferably 90% by mass or more, and may be 100% by mass. If the combined amount is less than 80% by mass, fuel economy may be poor.

Examples of materials that can be used in the rubber component, other than polyisoprene rubbers and BR include styrene-butadiene copolymer rubber (SBR), butadiene-isoprene copolymer rubber, and butyl rubber. Other examples include ethylene-propylene copolymer and ethylene-octene copolymer. Two or more types of these rubber materials may be used in combination.

The rubber composition according to the present invention contains a farnesene resin. The term "farnesene resin" herein refers to a polymer obtained by polymerizing farnesene as a monomer component. Farnesene exists in isomer forms, such as α-farnesene ((3E,7E)-3,7,11-trimethyl-1,3,6,10-dodecatetraene) or β-farnesene (7,11-dimethyl-3-methylene-1,6,10-dodecatriene). It is preferably (E)-β-farnesene having the following structure:

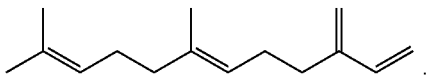

In the present invention, the farnesene resin can be added as a softener to improve processability, fuel economy, rubber strength, and abrasion resistance. The farnesene resin may be added in place of a conventional softener such as oil, or may be added in addition to a softener. In such cases, the effect of the present invention can be more suitably achieved.

The farnesene resin may be a homopolymer of farnesene (farnesene homopolymer) or may be a copolymer of farnesene and a vinyl monomer (farnesene-vinyl monomer copolymer). Examples of vinyl monomers include aromatic vinyl compounds such as styrene, 2-methylstyrene, 3-methylstyrene, 4-methylstyrene, α-methylstyrene, 2,4-dimethylstyrene, 2,4-diisopropylstyrene, 4-tert-butylstyrene, 5-t-butyl-2-methylstyrene, vinylethylbenzene, divinylbenzene, trivinylbenzene, divinylnaphthalene, tert-butoxystyrene, vinylbenzyldimethylamine, (4-vinylbenzyl)dimethylaminoethyl ether, N,N-dimethylaminoethylstyrene, N,N-dimethylaminomethylstyrene, 2-ethylstyrene, 3-ethylstyrene, 4-ethylstyrene, 2-t-butylstyrene, 3-t-butylstyrene, 4-t-butylstyrene, vinylxylene, vinylnaphthalene, vinyltoluene, vinylpyridine, diphenylethylene, and tertiary amino group-containing diphenylethylene; and conjugated diene compounds such as butadiene and isoprene. Styrene and butadiene are especially preferred. In other words, the farnesene-vinyl monomer copolymer is preferably a copolymer of farnesene and styrene (farnesene-styrene copolymer) or a copolymer of farnesene and butadiene (farnesene-butadiene copolymer). The use of the farnesene-styrene copolymer can enhance the effects of improving rubber strength and abrasion resistance, and particularly rubber strength. The use of the farnesene-butadiene copolymer can enhance the effect of improving rubber strength.

The farnesene homopolymer preferably has a glass transition temperature (Tg) of −60° C. or lower, more preferably −70° C. or lower, but preferably −120° C. or higher, more preferably −110° C. or higher. Farnesene homopolymers having a glass transition temperature within the range mentioned above can be suitably used as softeners for tires and fuel economy enhancers.

For the same reason, the farnesene-styrene copolymer preferably has a Tg of −15° C. or lower, more preferably −30° C. or lower, but preferably −80° C. or higher, more preferably −70° C. or higher.

For the same reason, the farnesene-butadiene copolymer preferably has a Tg of −60° C. or lower, more preferably −70° C. or lower, but preferably −120° C. or higher, more preferably −110° C. or higher.

The Tg values are measured using a differential scanning calorimeter (Q200, available from TA Instruments Japan) at a temperature increase rate of 10° C./min in conformity with JIS K 7121:1987.

The farnesene homopolymer preferably has a weight average molecular weight (Mw) of 3,000 or higher, more preferably 5,000 or higher, still more preferably 8,000 or higher. If the Mw is lower than 3,000, abrasion resistance tends to be poor. The Mw is also preferably 500,000 or lower, more preferably 300,000 or lower, still more preferably 150,000 or lower. If the Mw is higher than 500,000, processability and abrasion resistance tend to be poor.

Moreover, the farnesene-vinyl monomer copolymer preferably has a Mw of 3,000 or higher, more preferably 5,000 or higher, still more preferably 8,000 or higher. If the Mw is lower than 3,000, abrasion resistance tends to be poor. The Mw is also preferably 500,000 or lower, more preferably 300,000 or lower, still more preferably 150,000 or lower, particularly preferably 100,000 or lower. If the Mw is higher than 500,000, processability and abrasion resistance tend to be poor.

Farnesene homopolymers and farnesene-vinyl monomer copolymers having a Mw within the respective ranges mentioned above are in the liquid state at room temperature and can be suitably used as softeners for tires and fuel economy enhancers.

The farnesene homopolymer preferably has a melt viscosity of 1,000 Pa·s or lower, more preferably 200 Pa·s or lower, but preferably 0.1 Pa·s or higher, more preferably 0.5 Pa·s or higher. Farnesene homopolymers having a melt viscosity within the range mentioned above can be suitably used as softeners for tires and fuel economy enhancers, and are also excellent in bloom resistance.

For the same reason, the farnesene-vinyl monomer copolymer preferably has a melt viscosity of 1000 Pa·s or lower, more preferably 650 Pa·s or lower, still more preferably 200 Pa·s or lower, but preferably 1 Pa·s or higher, more preferably 5 Pa·s or higher.

The melt viscosity values are measured at 38° C. using a Brookfield-type viscometer available from BROOKFIELD ENGINEERING LABS. INC.

The farnesene homopolymer preferably has a farnesene content of 80% by mass or more, more preferably 90% by mass or more, based on 100% by mass of monomer components. The farnesene content may be 100% by mass.

The farnesene-vinyl monomer copolymer preferably has a combined content of farnesene and vinyl monomer of 80% by mass or more, more preferably 90% by mass or more, based on 100% by mass of monomer components. The combined content may be 100% by mass. Moreover, the farnesene/vinyl monomer copolymerization ratio, farnesene:vinyl monomer, is preferably 99/1 to 25/75, more preferably 80/20 to 40/60 by mass.

The farnesene resin may be synthesized by known methods. For example, in the case of synthesis by anion polymerization, hexane, farnesene, and sec-butyllithium, and optionally a vinyl monomer are charged into a sufficiently nitrogen-purged, pressure-resistant vessel; the mixture is then warmed, and stirred for several hours; and the resulting polymerization solution is quenched and then dried in vacuo, whereby a liquid farnesene resin can be obtained.

The procedure for polymerization in the preparation of the farnesene homopolymer is not particularly limited. For example, all the monomers may be polymerized at once, or the monomers may be sequentially added and polymerized. The procedure for copolymerization in the preparation of the farnesene-vinyl monomer copolymer is also not particularly limited. For example, all the monomers may be random-copolymerized at once; or specific monomer(s) (for example, farnesene monomer alone, or butadiene monomer alone) may previously be polymerized before the remaining monomer(s) is added and copolymerized therewith; or each specific monomer may previously be polymerized before the resulting polymers are block-copolymerized.

The farnesene used in the farnesene resin may be prepared from petroleum resources by chemical synthesis, or may be extracted from insects such as Aphididae or plants such as apples. It is preferably prepared by culturing a microorganism using a carbon source derived from a saccharide. The farnesene resin can be efficiently prepared from such farnesene.

The saccharide may be any of monosaccharides, disaccharides, and polysaccharides, or may be a combination thereof. Examples of monosaccharides include glucose, galactose, mannose, fructose, and ribose. Examples of disaccharides include sucrose, lactose, maltose, trehalose, and cellobiose. Examples of polysaccharides include starch, glycogen, cellulose, and chitin.

Saccharides suitable for preparing farnesene can be obtained from a wide variety of materials, such as sugar cane, bagasse, Miscanthus, sugar beet, sorghum, grain sorghum, switchgrass, barley, hemp, kenaf, potato, sweet potato, cassava, sunflower, fruits, molasses, whey, skim milk, corn, straw, grain, wheat, wood, paper, wheat straw, and cotton. Cellulosic wastes and other biomass materials may also be used. Preferred among these are plants of genus *Saccharum* such as sugar cane (*Saccharum officinarum*), with sugar cane being more preferred.

The microorganism may be any microorganism capable of producing farnesene through culture. Examples thereof include eukaryotes, bacteria, and archaebacteria. Examples of eukaryotes include yeast and plants.

The microorganism may be a transformant. The transformant can be obtained by introducing a foreign gene into a host microorganism. The foreign gene is preferably, but not limited to, a foreign gene involved in the production of farnesene because it can further improve farnesene production efficiency.

The conditions for culture are not particularly limited as long as they allow the microorganism to produce farnesene. The medium used for culturing the microorganism may be any medium commonly used for culturing microorganisms. Specific examples include, in the case of bacteria, KB medium and LB medium; in the case of yeast, YM medium, KY medium, F101 medium, YPD medium, and YPAD medium; and in the case of plants, basal media such as White medium, Heller medium, SH medium (Schenk and Hildebrandt medium), MS medium (Murashige and Skoog medium), LS medium (Linsmaier and Skoog medium), Gamborg medium, B5 medium, MB medium, and WP medium (for woody plants).

The culture temperature is preferably 0° C. to 50° C., more preferably 10° C. to 40° C., still more preferably 20° C. to 35° C., depending on the type of microorganism. The pH is preferably 3 to 11, more preferably 4 to 10, still more preferably 5 to 9. The microorganism may be cultured either anaerobically or aerobically depending on its type.

The microorganism may be cultured in a batch process, or in a continuous process using a bioreactor. Specific examples of the culturing method include shaking culture and rotary culture. Farnesene may be accumulated in the cells of the microorganism, or may be produced and accumulated in the culture supernatant.

In the case of recovering farnesene from the cultured microorganism, after the microorganism is collected by centrifugation and then disrupted, farnesene can be extracted from the disrupted solution with a solvent such as 1-butanol. Such solvent extraction may appropriately be combined with a known purification process such as chromatography. The microorganism is preferably disrupted at a low temperature, for example at 4° C., in order to prevent modification and breakdown of farnesene. The microorganism may be physically disrupted using glass beads, for example.

In the case of recovering farnesene from the culture supernatant, after the culture is centrifuged to remove the cells, farnesene may be extracted from the resulting supernatant with a solvent such as 1-butanol.

Farnesene resins formed from such microorganism-derived farnesenes are available from the market. Examples of such farnesene homopolymers include KB-101 and KB-107, both available from KURARAY CO., LTD. Examples of such farnesene-styrene copolymers include FSR-221, FSR-242, FSR-251, and FSR-262, all available from KURARAY CO., LTD. Examples of such farnesene-butadiene copolymers include FBR-746, FB-823, and FB-884, all available from KURARAY CO., LTD.

The amount of the farnesene resin per 100 parts by mass of the rubber component is 1 part by mass or more, preferably 2 parts by mass or more, more preferably 3 parts by mass or more. If the amount is less than 1 part by mass, the farnesene resin tends not to sufficiently exert its property-improving effect. Also, the amount of the farnesene resin is 20 parts by mass or less, preferably 10 parts by mass or less, more preferably 8 parts by mass or less. More than 20 parts by mass of the farnesene resin tends to result in deterioration in fuel economy, rubber strength, and abrasion resistance.

The rubber composition according to the present invention contains a reinforcing filler. Examples of reinforcing fillers include carbon black, silica, calcium carbonate, talc, alumina, clay, aluminum hydroxide, and mica. In particular, the rubber composition preferably contains carbon black and/or silica.

Examples of silica include dry silica (anhydrous silica) and wet silica (hydrous silica). Wet silica is preferred as it has more silanol groups.

The silica preferably has a nitrogen adsorption specific surface area ($N_2SA$) of 50 $m^2/g$ or greater, more preferably 60 $m^2/g$ or greater, still more preferably 100 $m^2/g$ or greater, particularly preferably 170 $m^2/g$ or greater. Silica with an $N_2SA$ of smaller than 50 $m^2/g$ tends to have a small reinforcing effect, resulting in reduced abrasion resistance and reduced rubber strength. The $N_2SA$ is also preferably 250 $m^2/g$ or smaller, more preferably 220 $m^2/g$ or smaller, still more preferably 200 $m^2/g$ or smaller. Silica with an $N_2SA$ of greater than 250 $m^2/g$ tends to poorly disperse, resulting in poor fuel economy and poor processability.

The $N_2SA$ of silica is determined in conformity with ASTM D1993-03.

In the case of the rubber composition containing silica, the amount of silica per 100 parts by mass of the rubber component is preferably 10 parts by mass or more, more preferably 20 parts by mass or more. If the amount is less than 10 parts by mass, silica tends to insufficiently exert its effect, resulting in reduced abrasion resistance and reduced rubber strength. The amount of silica is also preferably 60 parts by mass or less, more preferably 50 parts by mass or less. More than 60 parts by mass of silica tends to result in poor processability.

Examples of carbon black include furnace black (furnace carbon black) such as SAF, ISAF, HAF, MAF, FEF, SRF, GPF, APF, FF, CF, SCF, and ECF; acetylene black (acetylene carbon black); thermal black (thermal carbon black) such as FT and MT; channel black (channel carbon black) such as EPC, MPC, and CC; and graphite. These may be used alone or in combination of two or more.

The carbon black typically has a nitrogen adsorption specific surface area ($N_2SA$) of 5 to 200 $m^2/g$. The lower limit of the $N_2SA$ is preferably 50 $m^2/g$, more preferably 80 $m^2/g$, still more preferably 100 $m^2/g$, particularly preferably 110 $m^2/g$, while the upper limit thereof is preferably 150 $m^2/g$, more preferably 120 $m^2/g$. Moreover, the dibutyl phthalate (DBP) absorption of carbon black is typically 5 to 300 ml/100 g. The lower limit thereof is preferably 80 ml/100 g, while the upper limit is preferably 180 ml/100 g, more preferably 150 ml/100 g, still more preferably 120 ml/100 g. Carbon black with an $N_2SA$ or DBP absorption lower than the lower limit of the range mentioned above tends to have a small reinforcing effect, resulting in reduced abrasion resistance and reduced rubber strength. Carbon black with an $N_2SA$ or DBP absorption higher than the upper limit of the range mentioned above tends to poorly disperse and increase hysteresis loss, resulting in lower fuel economy and lower processability. The nitrogen adsorption specific surface area is determined in conformity with ASTM D4820-93. The DBP absorption is determined in conformity with ASTM D2414-93.

In the case of the rubber composition containing carbon black, the amount of carbon black per 100 parts by mass of the rubber component is preferably 5 parts by mass or more, more preferably 10 parts by mass or more, still more preferably 20 parts by mass or more. The amount of carbon black is also preferably 50 parts by mass or less, more preferably 40 parts by mass or less. When the amount is within the range mentioned above, the effect of the present invention can be well achieved.

The amount of the reinforcing filler per 100 parts by mass of the rubber component is 10 parts by mass or more, preferably 30 parts by mass or more, more preferably 40 parts by mass or more, still more preferably 50 parts by mass or more. If the amount is less than 10 parts by mass, fuel economy, rubber strength, and abrasion resistance may be poor. Also, the amount of the reinforcing filler is 60 parts by mass or less, preferably 55 parts by mass or less. If the amount is more than 60 parts by mass, reinforcement tends to be poor, resulting in reduced rubber strength and reduced abrasion resistance.

Other known additives may also be used. Examples include vulcanizing agents such as sulfur; vulcanization accelerators such as thiazole vulcanization accelerators, thiuram vulcanization accelerators, sulfenamide vulcanization accelerators, and guanidine vulcanization accelerators; vulcanization activators such as stearic acid and zinc oxide; organic peroxides; silane coupling agents; softeners such as oil; wax; and antioxidants.

Examples of sulfur include powdered sulfur, precipitated sulfur, colloidal sulfur, insoluble sulfur, and highly dispersible sulfur. The amount of sulfur per 100 parts by mass of the rubber component is preferably 0.1 to 15 parts by mass, more preferably 0.3 to 10 parts by mass, still more preferably 0.5 to 5 parts by mass.

Examples of vulcanization accelerators include thiazole vulcanization accelerators such as 2-mercaptobenzothiazole, dibenzothiazyldisulfide, and N-cyclohexyl-2-benzothiazyl-sulfenamide; thiuram vulcanization accelerators such as tetramethylthiuram monosulfide and tetramethylthiuram disulfide; sulfenamide vulcanization accelerators such as N-cyclohexyl-2-benzothiazolesulfenamide, N-t-butyl-2-benzothiazolesulfenamide, N-oxyethylene-2-benzothiazole-sulfenamide, N-oxyethylene-2-benzothiazolesulfenamide, and N,N'-diisopropyl-2-benzothiazolesulfenamide; and guanidine vulcanization accelerators such as diphenylguanidine, diorthotolylguanidine, and orthotolylbiguanidine. The amount thereof per 100 parts by mass of the rubber component is preferably 0.1 to 5 parts by mass, more preferably 0.2 to 3 parts by mass.

Examples of silane coupling agents include bis(3-triethoxysilylpropyl)tetrasulfide, bis(3-triethoxysilylpropyl) trisulfide, bis(3-triethoxysilylpropyl)disulfide, bis(2-triethoxysilylethyl)tetrasulfide, bis(3-trimethoxysilylpropyl) tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetra sulfide, 2-triethoxysilylethyl-N, N-dimethylthiocarbamoyltetrasulfide, 3-trimethoxysilylpropylbenzothiazoletetrasulfide, 3-triethoxysilylpropylbenzothiazolyltetrasulfide, 3-triethoxysilylpropylmethacrylatemonosulfide, 3-trimethoxysilylpropylmethacrylatemonosulfide, bis(3-diethoxymethylsilylpropyl)tetrasulfide, 3-mercaptopropyldimethoxymethylsilane, dimethoxymethylsilylpropyl-N,N-dimethylthiocarbamoyltetrasulfide, and dimethoxymethylsilylpropylbenzothiazoletetrasulfide. In view of the reinforcement-improving effect and the like, bis(3-triethoxysilylpropyl)tetrasulfide is preferred among these. These silane coupling agents may be used alone or in combination of two or more.

In the case of the rubber composition containing a silane coupling agent, the amount of silane coupling agent per 100 parts by mass of silica is preferably 1 part by mass or more, more preferably 3 parts by mass or more. With less than 1 part by mass of silane coupling agent, the viscosity of the unvulcanized rubber composition may be too high to ensure good processability. The amount of silane coupling agent is also preferably 20 parts by mass or less, more preferably 10 parts by mass or less. More than 20 parts by mass of silane coupling agent tends to result in reduced rubber strength and reduced abrasion resistance.

Examples of oil include aromatic oil (viscosity-gravity constant (VGC): 0.900 to 1.049), naphthenic oil (VGC: 0.850 to 0.899), and paraffinic oil (VGC: 0.790 to 0.849). The oil preferably has a polycyclic aromatic content of less than 3% by mass, more preferably less than 1% by mass. The polycyclic aromatic content is measured in conformity with the Institute of Petroleum (IP, U.K.) 346/92 method. Moreover, the oil preferably has an aromatic compound content (CA) of 20% by mass or more. Two or more types of these oils may be used in combination.

The amount of the farnesene resin based on 100% by mass of softeners is preferably 5% by mass or more, more preferably 10% by mass or more, still more preferably 30% by mass or more, particularly preferably 50% by mass or more, most preferably 60% by mass or more. The upper limit thereof may be 100% by mass but is preferably 80% by mass or less, more preferably 70% by mass or less. Moreover, the total softener amount, including the amount of the farnesene resin, per 100 parts by mass of the rubber component is preferably 1 to 20 parts by mass, more preferably 3 to 10 parts by mass, still more preferably 5 to 8 parts by mass.

The rubber composition may be prepared by known methods, such as, for example, by kneading the components using a known mixer such as a roll mill or a Banbury mixer. The rubber composition is used for cap treads of truck or bus tires.

Regarding the kneading conditions when additives other than vulcanizing agents and vulcanization accelerators are added, the kneading temperature is typically 50° C. to 200° C., preferably 80° C. to 190° C., and the kneading time is typically 30 seconds to 30 minutes, preferably 1 to 30 minutes.

When a vulcanizing agent and/or a vulcanization accelerator are added, the kneading temperature is typically 100° C. or lower, preferably in the range from room temperature to 80° C. Moreover, the composition containing a vulcanizing agent and/or a vulcanization accelerator is typically vulcanized, for example press-vulcanized, before use. The vulcanization temperature is typically 120° C. to 200° C., preferably 140° C. to 180° C.

The truck or bus tires of the present invention may be produced by conventional methods using the above rubber composition. Specifically, the rubber composition containing additives as appropriate, before vulcanization, is extruded into the shape of a cap tread of a tire, formed on a tire building machine in a usual manner, and assembled with other tire components to build an unvulcanized tire, which is then heat-pressed in a vulcanizer, whereby a truck or bus tire of the present invention can be produced.

EXAMPLES

The present invention will be specifically described referring to, but not limited to, examples.

The chemicals used in the examples and comparative examples are listed below.

Natural rubber: RSS#3
Polybutadiene rubber: UBEPOL BR150B (cis content: 97% by mass) available from Ube Industries, Ltd.
Silica: Ultrasil VN3 ($N_2SA$: 175 m$^2$/g) available from Degussa
Silane coupling agent: Si69 (bis(3-triethoxysilylpropyl) tetrasulfide) available from Degussa
Carbon black: DIABLACK N220 ($N_2SA$: 112 m$^2$/g, DBP absorption: 115 ml/100 g) available from Mitsubishi Chemical Corp.
Oil: X-140 (aromatic oil) available from Japan Energy Corp.
Farnesene homopolymer 1: KB-101 (Mw: 10,000, melt viscosity: 0.7 Pa·s, Tg: −72° C.) available from KURARAY CO., LTD.
Farnesene homopolymer 2: KB-107 (Mw: 135,000, melt viscosity: 69 Pa·s, Tg: −71° C.) available from KURARAY CO., LTD.
Farnesene-styrene copolymer 1: FSR-221 (Mw: 10,000, copolymerization ratio by mass: farnesene/styrene=77/23, melt viscosity: 5.7 Pa·s, Tg: −54° C.) available from KURARAY CO., LTD.
Farnesene-styrene copolymer 2: FSR-242 (Mw: 10,000, copolymerization ratio by mass: farnesene/styrene=60/40, melt viscosity: 59.2 Pa·s, Tg: −35° C.) available from KURARAY CO., LTD.
Farnesene-butadiene copolymer 1: FBR-746 (Mw: 100,000, copolymerization ratio by mass: farnesene/butadiene=60/40, melt viscosity: 603 Pa·s, Tg: −78° C.) available from KURARAY CO., LTD.
Farnesene-butadiene copolymer 2: FB-823 (Mw: 50,000, copolymerization ratio by mass: farnesene/butadiene=80/20, melt viscosity: 13 Pa·s, Tg=−78° C.) available from KURARAY CO., LTD.
Antioxidant: Nocrac 6C (N-(1,3-dimethylbutyl)-N'-phenyl-p-phenylenediamine) available from Ouchi Shinko Chemical Industrial Co., Ltd.
Stearic acid: stearic acid beads "Tsubaki" available from NOF Corporation
Zinc oxide: zinc oxide #1 available from Mitsui Mining & Smelting Co., Ltd.
Wax: SUNNOC N available from Ouchi Shinko Chemical Industrial Co., Ltd.
Sulfur: powdered sulfur available from Tsurumi Chemical Industry Co., Ltd.
Vulcanization accelerator: SOXINOL CZ available from Sumitomo Chemical Co., Ltd.

Examples and Comparative Examples

According to the formulations shown in Tables 1 to 3, the materials other than the sulfur and vulcanization accelerator were kneaded for five minutes at 150° C. using a 1.7-L Banbury mixer available from Kobe Steel, Ltd. to give a kneaded mixture. The sulfur and vulcanization accelerator were then added to the kneaded mixture, and the mixture was kneaded for five minutes at 80° C. using an open roll mill, providing an unvulcanized rubber composition. The unvulcanized rubber composition was press-vulcanized for 30 minutes at 150° C. using a 0.5 mm thick mold to prepare a vulcanized rubber composition. Separately, the unvulcanized rubber composition was formed into a tread shape and then assembled with other tire components on a tire building machine to build an unvulcanized tire. The unvulcanized tire was vulcanized for 30 minutes at 150° C., thereby providing a test tire having a size of 11R22.5.

The unvulcanized rubber compositions, vulcanized rubber compositions, and test tires thus prepared were evaluated as follows. Tables 1 to 3 show the results.
<Test Items and Test Methods>
<Processability Index>
The Mooney viscosity ($ML_{1+4}$/130° C.) of the unvulcanized rubber compositions was determined in conformity with JIS K 6300-1:2001 "Rubber, unvulcanized—Physical property—Part 1: Determination of Mooney viscosity and pre-vulcanization characteristics with Mooney viscometer". A Mooney viscosity tester was preheated for 1 minute to 130° C., and a small rotor was rotated under this temperature condition. After 4-minute rotation, Mooney viscosity ($ML_{1+4}$/130° C.) was measured. The measured values are expressed as an index using the equation below. A higher index indicates a lower Mooney viscosity and better processability (kneading processability), which in turn indicates higher tire productivity.

(Processability index)=(Mooney viscosity of Comparative Example 1)/(Mooney viscosity of each formulation)×100

<Fuel Economy Index>

Strip specimens having a size of 1 mm or 2 mm in width and 40 mm in length were punched out of sheets of the vulcanized rubber compositions, and the specimens were tested. Using a spectrometer available from Ueshima Seisakusho Co., Ltd., the tan δ of the vulcanized rubber compositions was measured at a dynamic strain amplitude of 1%, a frequency of 10 Hz, and a temperature of 50° C. The measured values are expressed as an index using the equation below. A higher index indicates a lower rolling resistance and thus better fuel economy.

(Fuel economy index)=(tan δ of Comparative Example 1)/(tan δ of each formulation)×100

<Rubber Strength Index>

A tensile test was performed in conformity with JIS K 6251:2010 to measure elongation at break. The measurement results are expressed as an index according to the equation below. A higher index indicates higher rubber strength (elongation at break).

(Rubber strength index)=(Elongation at break of each formulation)/(Elongation at break of Comparative Example 1)×100

<Abrasion Resistance Index>

The test tires having a size of 11R22.5 were mounted on a Japan-made 2-D vehicle. After the vehicle was driven 50,000 km, the groove depth in the tire tread part was measured. The distance at which the tire groove depth decreased by 1 mm was calculated and expressed as an index according to the equation below. A higher index indicates better abrasion resistance.

(Abrasion resistance index)=(Distance of each formulation)/(Distance of Comparative Example 1)×100

TABLE 1

|  |  | Example | | | | Comparative Example | | | | | | | |
|---|---|---|---|---|---|---|---|---|---|---|---|---|---|
|  |  | 1 | 2 | 3 | 4 | 1 | 2 | 3 | 4 | 5 | 6 | 7 | 8 |
| Formulation (part(s) by mass) | Natural rubber | 80 | 80 | 80 | 80 | 80 | 80 | 80 | 80 | 80 | 80 | 80 | 80 |
|  | Polybutadiene rubber | 20 | 20 | 20 | 20 | 20 | 20 | 20 | 20 | 20 | 20 | 20 | 20 |
|  | Silica | 25 | 25 | 50 | 50 | 25 | 50 | 50 | — | 25 | 25 | 25 | 25 |
|  | Silane coupling agent | 2 | 2 | 4 | 4 | 2 | 4 | 4 | — | 2 | 2 | 2 | 2 |
|  | Carbon black | 30 | 30 | — | — | 30 | — | 30 | 5 | 30 | 30 | 30 | 30 |
|  | Oil | 3 | 3 | 3 | 3 | 3 | 3 | 3 | 3 | 3 | 3 | 3 | 3 |
|  | Farnesene homopolymer 1 | 5 | — | 5 | — | — | — | — | — | 25 | — | 0.5 | — |
|  | Farnesene homopolymer 2 | — | 5 | — | 5 | — | — | — | — | — | 25 | — | 0.5 |
|  | Antioxidant | 1.5 | 1.5 | 1.5 | 1.5 | 1.5 | 1.5 | 1.5 | 1.5 | 1.5 | 1.5 | 1.5 | 1.5 |
|  | Stearic acid | 2 | 2 | 2 | 2 | 2 | 2 | 2 | 2 | 2 | 2 | 2 | 2 |
|  | Zinc oxide | 2.5 | 2.5 | 2.5 | 2.5 | 2.5 | 2.5 | 2.5 | 2.5 | 2.5 | 2.5 | 2.5 | 2.5 |
|  | Wax | 1 | 1 | 1 | 1 | 1 | 1 | 1 | 1 | 1 | 1 | 1 | 1 |
|  | Sulfur | 1.5 | 1.5 | 1.5 | 1.5 | 1.5 | 1.5 | 1.5 | 1.5 | 1.5 | 1.5 | 1.5 | 1.5 |
|  | Vulcanization accelerator | 2 | 2 | 2 | 2 | 2 | 2 | 2 | 2 | 2 | 2 | 2 | 2 |
| Evaluation | Processability index | 115 | 110 | 100 | 95 | 100 | 85 | 70 | 205 | 135 | 120 | 100 | 100 |
|  | Fuel economy index | 105 | 110 | 115 | 120 | 100 | 110 | 75 | 150 | 85 | 95 | 100 | 100 |
|  | Rubber strength index | 105 | 100 | 105 | 110 | 100 | 100 | 80 | 75 | 95 | 100 | 100 | 100 |
|  | Abrasion resistance index | 100 | 105 | 100 | 105 | 100 | 85 | 90 | 30 | 85 | 85 | 100 | 100 |

TABLE 2

|  |  | Example | | | | Comparative Example | | | | | | | |
|---|---|---|---|---|---|---|---|---|---|---|---|---|---|
|  |  | 5 | 6 | 7 | 8 | 1 | 2 | 3 | 4 | 9 | 10 | 11 | 12 |
| Formulation (part(s) by mass) | Natural rubber | 80 | 80 | 80 | 80 | 80 | 80 | 80 | 80 | 80 | 80 | 80 | 80 |
|  | Polybutadiene rubber | 20 | 20 | 20 | 20 | 20 | 20 | 20 | 20 | 20 | 20 | 20 | 20 |
|  | Silica | 25 | 25 | 50 | 50 | 25 | 50 | 50 | — | 25 | 25 | 25 | 25 |
|  | Silane coupling agent | 2 | 2 | 4 | 4 | 2 | 4 | 4 | — | 2 | 2 | 2 | 2 |
|  | Carbon black | 30 | 30 | — | — | 30 | — | 30 | 5 | 30 | 30 | 30 | 30 |
|  | Oil | 3 | 3 | 3 | 3 | 3 | 3 | 3 | 3 | 3 | 3 | 3 | 3 |
|  | Farnesene-styrene copolymer 1 | 5 | — | 5 | — | — | — | — | — | 25 | — | 0.5 | — |
|  | Farnesene-styrene copolymer 2 | — | 5 | — | 5 | — | — | — | — | — | 25 | — | 0.5 |
|  | Antioxidant | 1.5 | 1.5 | 1.5 | 1.5 | 1.5 | 1.5 | 1.5 | 1.5 | 1.5 | 1.5 | 1.5 | 1.5 |
|  | Stearic acid | 2 | 2 | 2 | 2 | 2 | 2 | 2 | 2 | 2 | 2 | 2 | 2 |
|  | Zinc oxide | 2.5 | 2.5 | 2.5 | 2.5 | 2.5 | 2.5 | 2.5 | 2.5 | 2.5 | 2.5 | 2.5 | 2.5 |
|  | Wax | 1 | 1 | 1 | 1 | 1 | 1 | 1 | 1 | 1 | 1 | 1 | 1 |
|  | Sulfur | 1.5 | 1.5 | 1.5 | 1.5 | 1.5 | 1.5 | 1.5 | 1.5 | 1.5 | 1.5 | 1.5 | 1.5 |
|  | Vulcanization accelerator | 2 | 2 | 2 | 2 | 2 | 2 | 2 | 2 | 2 | 2 | 2 | 2 |

TABLE 2-continued

|  |  | Example | | | | Comparative Example | | | | | | | |
|---|---|---|---|---|---|---|---|---|---|---|---|---|---|
|  |  | 5 | 6 | 7 | 8 | 1 | 2 | 3 | 4 | 9 | 10 | 11 | 12 |
| Evaluation | Processability index | 110 | 105 | 95 | 90 | 100 | 85 | 70 | 205 | 125 | 110 | 100 | 100 |
|  | Fuel economy index | 100 | 105 | 110 | 115 | 100 | 110 | 75 | 150 | 80 | 90 | 100 | 100 |
|  | Rubber strength index | 115 | 110 | 115 | 120 | 100 | 100 | 80 | 75 | 100 | 105 | 100 | 100 |
|  | Abrasion resistance index | 100 | 105 | 100 | 105 | 100 | 85 | 90 | 30 | 80 | 80 | 100 | 100 |

TABLE 3

|  |  | Example | | | | Comparative Example | | | | | | | |
|---|---|---|---|---|---|---|---|---|---|---|---|---|---|
|  |  | 9 | 10 | 11 | 12 | 1 | 2 | 3 | 4 | 13 | 14 | 15 | 16 |
| Formulation (part(s) by mass) | Natural rubber | 80 | 80 | 80 | 80 | 80 | 80 | 80 | 80 | 80 | 80 | 80 | 80 |
|  | Polybutadiene rubber | 20 | 20 | 20 | 20 | 20 | 20 | 20 | 20 | 20 | 20 | 20 | 20 |
|  | Silica | 25 | 25 | 50 | 50 | 25 | 50 | 50 | — | 25 | 25 | 25 | 25 |
|  | Silane coupling agent | 2 | 2 | 4 | 4 | 2 | 4 | 4 | — | 2 | 2 | 2 | 2 |
|  | Carbon black | 30 | 30 | — | — | 30 | — | 30 | 5 | 30 | 30 | 30 | 30 |
|  | Oil | 3 | 3 | 3 | 3 | 3 | 3 | 3 | 3 | 3 | 3 | 3 | 3 |
|  | Farnesene-butadiene copolymer 1 | 5 | — | 5 | — | — | — | — | — | 25 | — | 0.5 | — |
|  | Farnesene-butadiene copolymer 2 | — | 5 | — | 5 | — | — | — | — | — | 25 | — | 0.5 |
|  | Antioxidant | 1.5 | 1.5 | 1.5 | 1.5 | 1.5 | 1.5 | 1.5 | 1.5 | 1.5 | 1.5 | 1.5 | 1.5 |
|  | Stearic acid | 2 | 2 | 2 | 2 | 2 | 2 | 2 | 2 | 2 | 2 | 2 | 2 |
|  | Zinc oxide | 2.5 | 2.5 | 2.5 | 2.5 | 2.5 | 2.5 | 2.5 | 2.5 | 2.5 | 2.5 | 2.5 | 2.5 |
|  | Wax | 1 | 1 | 1 | 1 | 1 | 1 | 1 | 1 | 1 | 1 | 1 | 1 |
|  | Sulfur | 1.5 | 1.5 | 1.5 | 1.5 | 1.5 | 1.5 | 1.5 | 1.5 | 1.5 | 1.5 | 1.5 | 1.5 |
|  | Vulcanization accelerator | 2 | 2 | 2 | 2 | 2 | 2 | 2 | 2 | 2 | 2 | 2 | 2 |
| Evaluation | Processability index | 110 | 105 | 95 | 90 | 100 | 85 | 70 | 205 | 125 | 110 | 100 | 100 |
|  | Fuel economy index | 110 | 115 | 120 | 125 | 100 | 110 | 75 | 150 | 90 | 100 | 100 | 100 |
|  | Rubber strength index | 105 | 100 | 105 | 110 | 100 | 100 | 80 | 75 | 95 | 100 | 100 | 100 |
|  | Abrasion resistance index | 105 | 110 | 105 | 110 | 100 | 85 | 90 | 30 | 90 | 90 | 100 | 100 |

Tables 1 to 3 show that the rubber compositions of the examples, which contained a specific rubber component and predetermined amounts of a reinforcing filler and a farnesene resin, achieved balanced improvements in processability, fuel economy, rubber strength, and abrasion resistance. This demonstrates that they allow pneumatic tires having a good balance of improved fuel economy, rubber strength, and abrasion resistance to be produced with high productivity.

The invention claimed is:

1. A truck or bus tire, comprising
a cap tread formed from a rubber composition,
the rubber composition comprising
a rubber component including 60 to 95% by mass of polyisoprene rubbers and 5 to 40% by mass of polybutadiene rubber, and, per 100 parts by mass of the rubber component,
10 to 60 parts by mass of a silica and
1 to 20 parts by mass of a farnesene resin obtained by polymerizing farnesene.
2. The truck or bus tire according to claim 1,
wherein the farnesene resin is a farnesene homopolymer.
3. The truck or bus tire according to claim 2,
wherein the homopolymer has a glass transition temperature of −60° C. or lower.
4. The truck or bus tire according to claim 2,
wherein the homopolymer has a weight average molecular weight of 3,000 to 500,000.
5. The truck or bus tire according to claim 2,
wherein the homopolymer has a melt viscosity at 38° C. of 1,000 Pa·s or lower.
6. The truck or bus tire according to claim 1,
wherein the farnesene resin is a copolymer of farnesene and a vinyl monomer.
7. The truck or bus tire according to claim 6,
wherein the vinyl monomer is styrene.
8. The truck or bus tire according to claim 6,
wherein the vinyl monomer is butadiene.
9. The truck or bus tire according to claim 6,
wherein the copolymer has a farnesene/vinyl monomer ratio of 99/1 to 25/75 by mass.
10. The truck or bus tire according to claim 6,
wherein the copolymer has a weight average molecular weight of 3,000 to 500,000.
11. The truck or bus tire according to claim 6,
wherein the copolymer has a melt viscosity at 38° C. of 1,000 Pa·s or lower.
12. The truck or bus tire according to claim 1,
wherein the farnesene is prepared by culturing a microorganism using a carbon source derived from a saccharide.

* * * * *